US011524986B2

(12) United States Patent
Holub et al.

(10) Patent No.: US 11,524,986 B2
(45) Date of Patent: Dec. 13, 2022

(54) PEPTIDE-BASED INHIBITORS OF GROWTH HORMONE ACTION AND METHODS OF USE THEREOF

(71) Applicant: Ohio University, Athens, OH (US)

(72) Inventors: Justin M. Holub, Athens, OH (US); John J. Kopchick, Athens, OH (US); Reetobrata Basu, Athens, OH (US)

(73) Assignee: Ohio University, Athens, OH (US)

( * ) Notice: Subject to any disclaimer, the term of this patent is extended or adjusted under 35 U.S.C. 154(b) by 0 days.

(21) Appl. No.: 17/258,934

(22) PCT Filed: Jul. 10, 2019

(86) PCT No.: PCT/US2019/041129
§ 371 (c)(1),
(2) Date: Jan. 8, 2021

(87) PCT Pub. No.: WO2020/014307
PCT Pub. Date: Jan. 16, 2020

(65) Prior Publication Data
US 2021/0122801 A1    Apr. 29, 2021

Related U.S. Application Data

(60) Provisional application No. 62/696,458, filed on Jul. 11, 2018.

(51) Int. Cl.
*A61K 38/00* (2006.01)
*C07K 14/61* (2006.01)

(52) U.S. Cl.
CPC .............. *C07K 14/61* (2013.01); *A61K 38/00* (2013.01)

(58) Field of Classification Search
CPC ................................ A61K 38/00; C07K 14/61
See application file for complete search history.

(56) References Cited

U.S. PATENT DOCUMENTS

| | | |
|---|---|---|
| 4,686,098 A | 8/1987 | Kopchick et al. |
| 4,828,987 A | 5/1989 | Kopchick et al. |
| 5,350,836 A | 9/1994 | Kopchick et al. |
| 5,401,829 A | 3/1995 | James et al. |
| 5,681,809 A | 10/1997 | Kopchick et al. |
| 5,700,671 A | 12/1997 | Prieto et al. |
| 5,750,176 A | 5/1998 | Prieto et al. |
| 5,864,008 A * | 1/1999 | James ............... C07K 14/005 530/324 |
| 5,891,698 A | 4/1999 | Prieto et al. |
| 5,892,070 A | 4/1999 | Prieto et al. |
| 5,958,879 A | 9/1999 | Kopchick et al. |
| 6,080,911 A | 6/2000 | Kopchick et al. |
| 6,204,431 B1 | 3/2001 | Prieto et al. |
| 6,238,915 B1 | 5/2001 | Chihara |
| 6,583,115 B1 | 6/2003 | Kopchick et al. |
| 6,787,336 B1 | 9/2004 | Kopchick et al. |
| 6,858,389 B1 | 2/2005 | Kopchick et al. |
| 7,060,437 B1 | 6/2006 | Kopchick et al. |
| 7,309,572 B2 | 12/2007 | Kopchick et al. |
| 8,962,811 B2 | 2/2015 | Kieliszewski et al. |
| 9,234,242 B2 | 1/2016 | Akil et al. |
| 9,422,545 B2 | 8/2016 | Zhang |
| 9,644,004 B2 | 5/2017 | Wang et al. |
| 9,814,760 B2 | 11/2017 | Bancel et al. |
| 2007/0142311 A1 | 6/2007 | Kopchick et al. |
| 2007/0154992 A1 | 7/2007 | DeFrees |
| 2009/0215676 A1 | 8/2009 | Van Der Lely |
| 2010/0028326 A1 | 2/2010 | Kopchick et al. |
| 2011/0066230 A1 | 3/2011 | Schally et al. |
| 2011/0300641 A1 | 12/2011 | Kopchick et al. |
| 2017/0304405 A1 | 10/2017 | Beckers et al. |

FOREIGN PATENT DOCUMENTS

| | | | |
|---|---|---|---|
| EP | 0284406 A1 | 9/1988 | |
| EP | 2356998 A1 * | 8/2011 | ............... A61P 7/02 |
| JP | H01502753 A | 9/1989 | |
| WO | 8807547 A1 | 10/1988 | |

OTHER PUBLICATIONS

PCT International Search Report and Written Opinion, Application No. PCT/US2019/041129, dated Oct. 4, 2019.
Japanese Office Action, Application No. 2021-500676, dated Mar. 22, 2022.
Wells, "Review Binding in the growth hormone receptor complex", Proc. Natl. Acad. Sci. USA, 1996, vol. 93, pp. 1-6. Retrieved from the Internet:URL:https://www.pnas.org/content/pnas/93/1/1.full.pdf [retrieved on Feb. 2, 2022].
Sundstroem et al., "Crystal Structure of an Antagonist Mutant of Human Growth Hormone, G120R, in Complex with Its Receptor at 2.9 A Resolution", The Journal of Biological Chemistry, 1996, vol. 271, No. 50, pp. 32197-32203.
Sattler, "Developing Synthetic Peptide-Based Inhibitors of Human Growth Hormone Receptor, Acknowledgements", 2018, XP055886727, http://rave.ohiolink.edu/etdc/view?acc_num=ouhonors1524838355466962.
Vos et al., "Human Growth Hormone and Extracellular Domain of Its Receptor: Crystal Structure of the Complex", Science, American Association for the Advancement of Science, US, 1992, vol. 255, pp. 306-312.
Basu et al., "A novel peptide antagonist of the human growth hormone receptor", Journal of Biological Chemistry, 2021, vol. 296, pp. 1-16.
The Extended European Search Report, Application No. 19834632.2, dated Feb. 17, 2022.

* cited by examiner

*Primary Examiner* — Aradhana Sasan
*Assistant Examiner* — Mercy H Sabila
(74) *Attorney, Agent, or Firm* — MacMillan, Sobanski & Todd, LLC

(57) ABSTRACT

Compositions and methods for the inhibiting human growth hormone (hGH), and treating or preventing hGH-mediated disorders, using a S1H peptide having the amino acid sequence of [SEQ ID NO: 1], or a variant thereof, are described.

17 Claims, 9 Drawing Sheets

Specification includes a Sequence Listing.

S1H (36-51) Ac-YIPKEQKYSFLQNPQT-NH$_2$

| SEQ. ID NO. | Peptide | Sequence | Mass (Da) | |
|---|---|---|---|---|
| | | | Calculated | Observed |
| 1 | 36-51 | YIPKEQKYSFLQNPQT | 2025.26 | 2026.04 |
| 2 | K39A | YIPAEQKYSFLQNPQT | 1968.99 | 1968.99 |
| 3 | E40A | YIPKAQKYSFLQNPQT | 1967.23 | 1967.03 |
| 4 | Q41A | YIPKEAKYSFLQNPQT | 1968.22 | 1968.02 |
| 5 | K42A | YIPKEQAYSFLQNPQT | 1967.18 | 1967.98 |
| 6 | Y43A | YIPKEQKASFLQNPQT | 1933.17 | 1933.02 |
| 7 | S44A | YIPKEQKYAFLQNPQT | 2010.50 | 2010.10 |
| 8 | F45A | YIPKEQKYSALQNPQT | 1950.15 | 1950.00 |
| 9 | L46A | YIPKEQKYSFAQNPQT | 1983.19 | 1983.00 |
| 10 | Q47A | YIPKEQKYSFLANPQT | 1968.22 | 1968.02 |
| 11 | N48A | YIPKEQKYSFLQAPQT | 1983.10 | 1983.00 |
| 12 | Human Growth Hormone | MFPTIPLSRLFDNAMLRAHRLHQLAFDTYQ EFEEAYIPKEQKYSFLQNPQTSLCFSESIPTP SNREETQQKSNLELLRISLLLIQSWLEPVQF LRSVFANSLVYGASDSNVYDLLKDLEEGIQT LMGRLEDGSPRTGQIFKQTYSKFDTNSHND DALLKNYGLLYCFRKDMDKVETFLRIVQC RSVEGSCGF | | |

FIG. 8

PEPTIDE-BASED INHIBITORS OF GROWTH HORMONE ACTION AND METHODS OF USE THEREOF

CROSS-REFERENCE TO RELATED APPLICATIONS

This application is a national stage application filed under 35 U.S.C. § 371 of international application PCT/US2019/041129, filed under the authority of the Patent Cooperation Treaty on Jul. 10, 2019, which claims the priority to U.S. Provisional Application Ser. No. 62/696,458 filed Jul. 11, 2018, the entire disclosures of which are expressly incorporated herein by reference.

STATEMENT REGARDING FEDERALLY SPONSORED RESEARCH

This invention was made with no government support. The government has no rights in this invention.

The instant application contains a Sequence Listing which has been submitted electronically in ASCII format and is hereby incorporated by reference in its entirety. The ASCII copy, created on Jun. 30, 2022 is named 3834_60264-WO-PCT_OU-18017_SL.txt and is 6,934 bytes in size.

BACKGROUND OF THE INVENTION

Human growth hormone (hGH) is a 191-amino acid peptide that serves as an important endocrine mediator by controlling many physiological actions in the body including cell growth, reproduction and regeneration. HGH contains four main helices (A-D) that are required for its functional interaction with the hGH receptor (hGHR). Excess hGH activity can result in the onset of acromegaly, a syndrome characterized by uncontrolled bone and organ growth. If left untreated, acromegaly can lead to thickening of bones and enlarged organs. Also, high levels of hGH have been implicated in several types of in cancer. Consequently, there is great interest in the development of molecules that can selectively inhibit hGH action.

Synthetic peptides offer a viable alternative to small molecules and large proteins to target therapeutically relevant protein-protein interactions. Indeed, peptide-based drugs occupy a unique "middle space" that facilitates their development as potential therapeutics. For example, peptides under 50 amino acids in length are easily synthesized and can be generated through chemical synthesis procedures in the laboratory. Furthermore, peptides can be engineered to mimic protein interaction domains that fold into stable three-dimensional structures, thus providing a scaffold from which to design potential inhibitors. Because of these unique properties, peptide-based molecules can, in theory, be developed to target nearly any biomolecular interaction.

It would be desirable to develop a highly selective inhibitor or antagonist of growth hormone action.

There is no admission that the background art disclosed in this section legally constitutes prior art.

SUMMARY OF THE INVENTION

In a first aspect, there is described herein an isolated or non-naturally occurring polypeptide comprising an amino acid sequence which is at least 50% identical with the amino acid sequence of S1H [SEQ ID NO:1], and differs therefrom solely in a substitution of a conservative replacement amino acid in the S1H peptide sequence.

In another aspect, there is described herein an isolated or non-naturally occurring polypeptide consisting of amino acid sequence of S1H action.

In another aspect, there is described herein a composition comprising S1H peptide, or a variant thereof that mimics a small, well-folded α-helix within human growth hormone (hGH).

In certain embodiments, the S1H peptide is a sequence mimetic of an area of hGH between residues 36-51 which is a region within Site 1 of hGH that interacts with the human growth hormone receptor (hGHR).

In certain embodiments, the S1H peptide comprises [SEQ ID NO: 1].

In certain embodiments, the composition further comprises a pharmaceutically acceptable excipient, diluent, adjuvant, or carrier.

In another aspect, there is described herein a method of therapeutics to combat human hGH mediated disease in a subject, the method comprising: administering to a subject an effective amount of a S1H peptide consisting of the amino acid sequence [SEQ ID NO: 1], or a variant thereof, to inhibit hGH action in the subject.

In another aspect, there is described herein a method of inhibiting hGH induced tyrosine phosphorylation of STAT5 in a subject, the method comprising: administering an effective amount of a S1H peptide consisting of the amino acid sequence [SEQ ID NO: 1], or a variant thereof, to inhibit phosphorylation of STAT5.

In another aspect, there is described herein a method of inhibiting human growth hormone (hGH) protein action in a subject, the method comprising: administering to a subject an effective amount of a S1H peptide consisting of the amino acid sequence [SEQ ID NO: 1], or a variant thereof, to inhibit an hGH protein in the subject.

In another aspect, there is described herein a method of treating, preventing, or ameliorating a hGH related disorder, the method comprising: administering to a subject in need thereof an effective amount of a S1H peptide consisting of the amino acid sequence [SEQ ID NO: 1], or a variant thereof, to treat, prevent, or ameliorate a hGH related disorder in the subject.

In another aspect, there is described herein a method for treating hGH action in a subject, the method comprising: administering a therapeutically effective amount of a peptide comprising a Site 1 helix peptide found in hGH to the subject, wherein the peptide inhibits hGH and is a hGH peptide mimetic.

In certain embodiments, the composition further includes a pharmaceutically acceptable excipient, diluent, adjuvant, or carrier.

In certain embodiments, the peptide is administered orally, nasally, topically, intravenously, intraperitoneally, intrathecally, or intracerebroventricularly.

In certain embodiments, the subject is a human.

In certain embodiments, the subject is a vertebrate.

In certain embodiments, the subject is a mammal.

In certain embodiments, the S1H peptide consists of SEQ ID NO:1.

In certain embodiments, the variant has at least 50% sequence identity to the amino acid sequence of S1H; wherein the variant has at least 60% sequence identity to the amino acid sequence of S1H; wherein the variant has at least 70% sequence identity to the amino acid sequence of S1H; wherein the variant has at least 80% sequence identity to the amino acid sequence of S1H; or, wherein the variant has at least 90% sequence identity to the amino acid sequence of S1H.

In certain embodiments, the hGH related disorder is one or more of: acromegaly; age-related macular degeneration; cancer; diabetes; gigantism, vascular eye diseases including diabetic retinopathy, retinopathy of prematurity, and retinopathy of sickle-cell anemia; nephropathy, diabetes induce nephropathy (glomerulosclerosis), neurodegeneration, and cancer.

In another aspect, there is described herein a use of a synthetic peptide to inhibit hGH action, wherein the synthetic peptide consists of the amino acid sequence [SEQ ID NO: 1], or a variant thereof.

In another aspect, there is described herein a use of a synthetic peptide to inhibit hGH action, wherein the synthetic peptide mimics the hGH between residues 36-51.

In certain embodiments, the preferred growth-inhibitory peptides are characterized by a modification of the surface topography of Site 1. It will be seen from FIGS. 1-2 that in the Site 1 helix of hGH, corresponds to residues 36-51 of the full-length hGH.

Another aspect, there is provided, methods for the treatment of various diseases involving the production of excess hGH, wherein the methods comprise the step of administering an effective amount of an hGH antagonist comprising S1H or a variant thereof.

Specifically, the methods include treating acromegaly, gigantism, cancer, diabetes, vascular eye diseases (diabetic retinopathy, retinopathy of prematurity, age-related macular degeneration, retinopathy of sickle-cell anemia, etc.) as well as nephropathy and neurodegeneration.

Various objects and advantages of this invention will become apparent to those skilled in the art from the following detailed description of the preferred embodiment, when read in light of the accompanying drawings.

BRIEF DESCRIPTION OF THE DRAWINGS

FIG. 8: Sequences and mass data for peptides described herein.

DETAILED DESCRIPTION OF THE INVENTION

Figure 1:
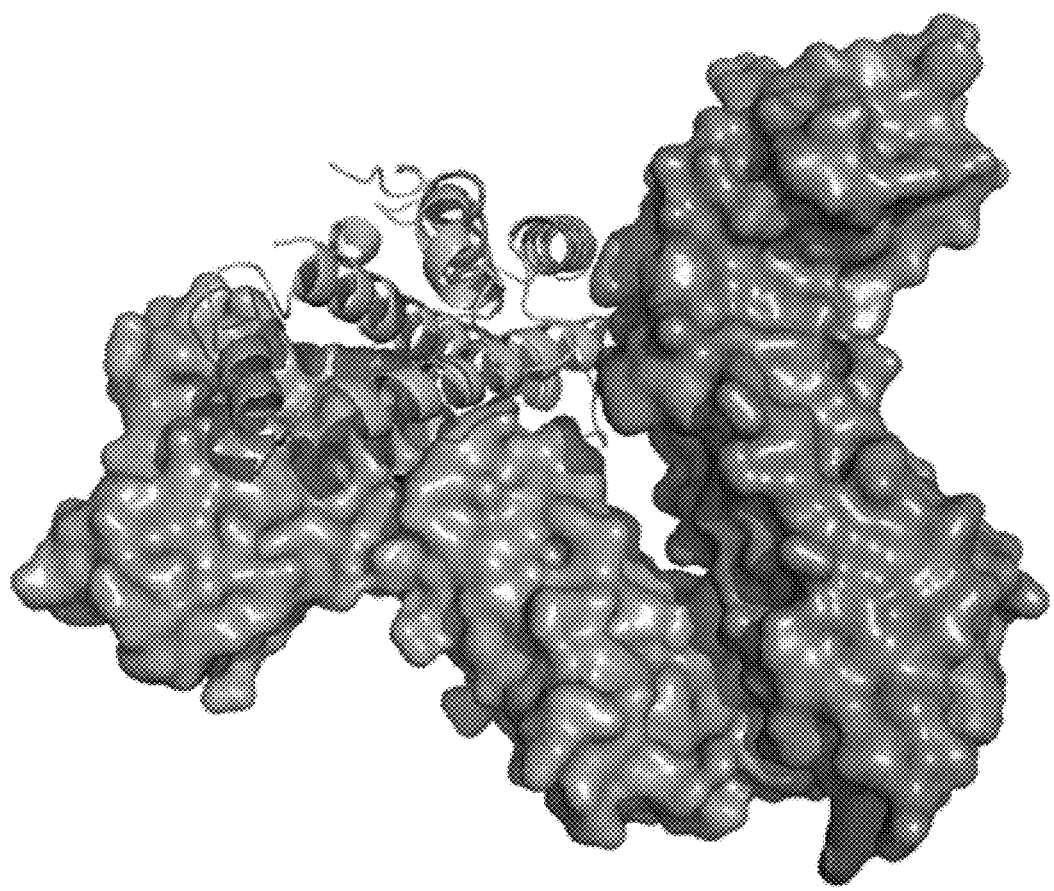
FIG. 1: Three-dimensional crystal structure of the hGH bound to dimerized hGH receptor: hGH (pink) is shown as a ribbon diagram bound to hGHR (grey). The site 1 helix of hGH is colored purple.

It should be understood at the outset that, although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described below. Additionally, unless otherwise specifically noted, articles depicted in the drawings are not necessarily drawn to scale.

Throughout this disclosure, various publications, patents, and published patent specifications are/may be referenced by an identifying citation. Such disclosures of these publications, patents, and published patent specifications are hereby incorporated by reference into the present disclosure in their entirety to more fully describe the state of the art to which this invention pertains.

Definitions

In order to facilitate review of the various embodiments of the disclosure, the following explanations of specific terms are provided:

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like.

"Peptide" and "polypeptide" are used interchangeable herein. The peptide or polypeptide may be composed of all natural amino acids or various non-natural amino acids, and may include PTMs, cyclic peptides, and any fragment or variant thereof. As used herein, a "nucleic acid" or "polynucleotide" includes a nucleic acid, an oligonucleotide, a nucleotide, a polynucleotide. The nucleic acid or polynucleotide may be double-stranded, single-stranded, or triple-stranded DNA or RNA (including cDNA), or a DNA-RNA hybrid of genetic or synthetic origin, wherein the nucleic acid contains any combination of deoxyribonucleotides and ribonucleotides and any combination of bases, including, but not limited to, adenine, thymine, cytosine, guanine, uracil, inosine, and xanthine hypoxanthine. The nucleic acid or polynucleotide may be combined with a carbohydrate, lipid, protein, or other materials. Preferably, the nucleic acid encodes the protein.

As used herein, the "complement" of a nucleic acid refers, herein, to a nucleic acid molecule with sufficient homology to recognize, or which will hybridize to another nucleic acid under conditions of high stringency. High-stringency conditions are known in the art (see e.g., Maniatis et al., Molecular Cloning: A Laboratory Manual, 2nd ed. (Cold Spring Harbor: Cold Spring Harbor Laboratory, 1989) and Ausubel et al., eds., Current Protocols in Molecular Biology (New York, N.Y.: John Wiley & Sons, Inc., 2001)). Stringent conditions are sequence-dependent, and may vary depending upon the circumstances. As used herein, the term "cDNA" refers to an isolated DNA polynucleotide or nucleic acid molecule derived from an mRNA or RNA molecule, or any fragment, derivative, or complement thereof. It may be double-stranded, single-stranded, or triple-stranded, it may have originated recombinantly or synthetically, and it may represent coding and/or noncoding 5' and/or 3' sequences.

In addition, "complementary" means not only those that are completely complementary to a region of at least 15 continuous nucleotides, but also those that have a nucleotide sequence homology of at least 40% in certain instances, 50% in certain instances, 60% in certain instances, 70% in certain instances, at least 80%, 90%, and 95% or higher. The degree of homology between nucleotide sequences can be determined by various methods, including an algorithm, BLAST, etc.

As used herein, nucleic acids and/or nucleic acid sequences are "homologous" when they are derived, naturally or artificially, from a common ancestral nucleic acid or nucleic acid sequence. Homology is generally inferred from sequence identity between two or more nucleic acids or proteins (or sequences thereof). The precise percentage of identity between sequences that is useful in establishing homology varies with the nucleic acid and protein at issue to establish homology. Higher levels of sequence identity, e.g., 30%, 40%, 50%, 60%, 70%, 80%, 90%, 95%, 96%, 97%, 98%, or 99% or more can also be used to establish homology. Methods for determining sequence similarity percentages (e.g., BLASTN using default parameters) are generally available. Software for performing BLAST analyses is publicly available through the National Center for Biotechnology Information.

In some embodiments "variant mimics" are provided. As used herein, the term "variant mimic" is one which contains one or more amino acids which would mimic an activated sequence. Alternatively, variant mimics may result in deactivation or in an inactivated product containing the mimic. Also contemplated are several types of compositions which are polypeptide based including variants and derivatives. These include substitutional, insertional, deletion and covalent variants and derivatives. The term "derivative" is used synonymously with the term "variant" but generally refers to a molecule that has been modified and/or changed in any way relative to a reference molecule or starting molecule.

As such, encoding polypeptides containing substitutions, insertions and/or additions, deletions and covalent modifications with respect to reference sequences, in particular the polypeptide sequences disclosed herein, are included within the scope of this invention. For example, sequence tags or amino acids, such as one or more lysines, can be added to the peptide sequences of the invention (e.g., at the N-terminal or C-terminal ends). Sequence tags can be used for peptide purification or localization. Lysines can be used to increase peptide solubility or to allow for biotinylation. Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence which is soluble, or linked to a solid support.

"Substitutional variants" when referring to polypeptides are those that have at least one amino acid residue in a native or starting sequence removed and a different amino acid inserted in its place at the same position. The substitutions may be single, where only one amino acid in the molecule has been substituted, or they may be multiple, where two or more amino acids have been substituted in the same molecule. Also, the substituted amino acid could be of the L or D versions.

As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between threonine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

"Insertional variants" when referring to polypeptides are those with one or more amino acids inserted immediately adjacent to an amino acid at a particular position in a native or starting sequence "Immediately adjacent" to an amino acid means connected to either the alpha-carboxy or alpha-amino functional group of the amino acid.

"Deletional variants" when referring to polypeptides are those with one or more amino acids in the native or starting amino acid sequence removed. Ordinarily, deletional variants will have one or more amino acids deleted in a particular region of the molecule.

"Covalent derivatives" when referring to polypeptides include modifications of a native or starting protein with an organic proteinaceous or non-proteinaceous derivatizing agent, and/or post-translational modifications. Covalent modifications are traditionally introduced by reacting targeted amino acid residues of the protein with an organic derivatizing agent that is capable of reacting with selected side-chains or terminal residues, or by harnessing mechanisms of post-translational modifications that function in selected recombinant host cells. The resultant covalent derivatives are useful in programs directed at identifying residues important for biological activity, for immunoassays, or for the preparation of anti-protein antibodies for immunoaffinity purification of the recombinant glycoprotein. Such modifications are within the ordinary skill in the art and are performed without undue experimentation.

"Substitutional variants" when referring to polypeptides are those that have at least one amino acid residue in a native or starting sequence removed and a different amino acid inserted in its place at the same position. This amino acid could have the L- or D-conformation. The substitutions may be single, where only one amino acid in the molecule has been substituted, or they may be multiple, where two or more amino acids have been substituted in the same molecule.

As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

"Insertional variants" when referring to polypeptides are those with one or more amino acids inserted immediately adjacent to an amino acid at a particular position in a native or starting sequence "Immediately adjacent" to an amino acid means connected to either the alpha-carboxy or alpha-amino functional group of the amino acid.

"Deletional variants" when referring to polypeptides are those with one or more amino acids in the native or starting amino acid sequence removed. Ordinarily, deletional variants will have one or more amino acids deleted in a particular region of the molecule.

"Covalent derivatives" when referring to polypeptides include modifications of a native or starting protein with an organic proteinaceous or non-proteinaceous derivatizing agent, and/or post-translational modifications. Covalent modifications are traditionally introduced by reacting targeted amino acid residues of the protein with an organic derivatizing agent that is capable of reacting with selected side-chains or terminal residues, or by harnessing mechanisms of post-translational modifications that function in selected recombinant host cells. The resultant covalent derivatives are useful in programs directed at identifying residues important for biological activity, for immunoassays, or for the preparation of anti-protein antibodies for immunoaffinity purification of the recombinant glycoprotein. Such modifications are within the ordinary skill in the art and are performed without undue experimentation.

"Features" when referring to polypeptides are defined as distinct amino acid sequence-based components of a molecule. Features of the polypeptides encoded include surface manifestations, local conformational shape, folds, loops, half-loops, domains, half-domains, sites, termini or any combination thereof.

As used herein when referring to polypeptides the term "surface manifestation" refers to a polypeptide based component of a protein appearing on an outermost, solvent-exposed surface.

As used herein when referring to polypeptides the term "local conformational shape" means a polypeptide based structural manifestation of a protein which is located within a definable space of the protein.

As used herein when referring to polypeptides the term "fold" refers to the resultant conformation of an amino acid sequence upon energy minimization. A fold may occur at the secondary or tertiary level of the folding process. Examples of secondary level folds include beta sheets and alpha helices. Examples of tertiary folds include domains and regions formed due to aggregation or separation of energetic forces. Regions formed in this way include hydrophobic and hydrophilic pockets, and the like.

As used herein the term "turn" as it relates to protein conformation means a bend which alters the direction of the backbone of a peptide or polypeptide and may involve one, two, three or more amino acid residues.

As used herein when referring to polypeptides the term "loop" refers to a structural feature of a polypeptide which may serve to reverse the direction of the backbone of a peptide or polypeptide. Where the loop is found in a polypeptide and only alters the direction of the backbone, it may comprise four or more amino acid residues. Loops may be open or closed. Closed loops or "cyclic" loops may comprise 2, 3, 4, 5, 6, 7, 8, 9, 10 or more amino acids between the bridging moieties. Such bridging moieties may comprise a cysteine-cysteine bridge (Cys-Cys) typical in polypeptides having disulfide bridges or alternatively bridging moieties may be non-protein based such as the dibromozylyl agents used herein. Cyclic peptides may also be generated by intramolecular cross-linking between non-natural amino acid side chains (i.e., olefin metathesis), head to tail (N to C-terminus) cyclization, or through hydrogen bond surrogates at the N- or C-terminus.

As used herein when referring to polypeptides the term "half-loop" refers to a portion of an identified loop having at least half the number of amino acid resides as the loop from which it is derived. It is understood that loops may not always contain an even number of amino acid residues. Therefore, in those cases where a loop contains or is identified to comprise an odd number of amino acids, a half-loop of the odd-numbered loop will comprise the whole number portion or next whole number portion of the loop (number of amino acids of the loop/2+/−0.5 amino acids). For example, a loop identified as a 7 amino acid loop could produce half-loops of 3 amino acids or 4 amino acids (7/2=3.5+/−0.5 being 3 or 4).

As used herein when referring to polypeptides the term "domain" refers to a motif of a polypeptide having one or more identifiable structural or functional characteristics or properties (e.g., binding capacity, serving as a site for protein-protein interactions).

As used herein when referring to polypeptides the term "half-domain" means a portion of an identified domain having at least half the number of amino acid resides as the domain from which it is derived. It is understood that domains may not always contain an even number of amino acid residues. Therefore, in those cases where a domain contains or is identified to comprise an odd number of amino acids, a half-domain of the odd-numbered domain will comprise the whole number portion or next whole number portion of the domain (number of amino acids of the domain/2+/−0.5 amino acids). For example, a domain identified as a 7 amino acid domain could produce half-domains of 3 amino acids or 4 amino acids (7/2=3.5+/−0.5 being 3 or 4). It is also understood that subdomains may be identified within domains or half-domains, these subdomains possessing less than all of the structural or functional properties identified in the domains or half domains from which they were derived. It is also understood that the amino acids that comprise any of the domain types herein need not be contiguous along the backbone of the polypeptide (i.e., nonadjacent amino acids may fold structurally to produce a domain, half-domain or subdomain).

As used herein when referring to polypeptides the terms "site" as it pertains to amino acid based embodiments is used synonymously with "amino acid residue" and "amino acid side chain." A site represents a position within a peptide or polypeptide that may be modified, manipulated, altered, derivatized or varied within the polypeptide based molecules of the present invention.

As used herein the terms "termini" or "terminus" when referring to polypeptides refers to an extremity of a peptide or polypeptide. Such extremity is not limited only to the first or final site of the peptide or polypeptide but may include additional amino acids in the terminal regions. The polypeptide based molecules of the present invention may be characterized as having both an N-terminus (terminated by an amino acid with a free amino group ($NH_2$) or capped by an acetyl group ($COCH_3$) or fluorophore) and a C-terminus (terminated by an amino acid with a free carboxyl group (COOH) or amide group ($CONH_2$)). Proteins of the invention are in some cases made up of multiple polypeptide chains brought together by disulfide bonds or by non-covalent forces (multimers, oligomers). These sorts of proteins will have multiple N- and C-termini. Alternatively, the termini of the polypeptides may be modified such that they begin or end, as the case may be, with a non-polypeptide based moiety such as an organic conjugate.

Once any of the features have been identified or defined as a desired component of a polypeptide to be encoded by the primary construct, any of several manipulations and/or modifications of these features may be performed by moving, swapping, inverting, deleting, randomizing or duplicating. Furthermore, it is understood that manipulation of features may result in the same outcome as a modification to the molecules. For example, a manipulation which involved deleting a domain would result in the alteration of the length of a molecule just as modification of a nucleic acid to encode less than a full length molecule would.

Modifications and manipulations can be accomplished by methods known in the art such as, but not limited to, site directed mutagenesis or peptide cyclization. The resulting modified molecules may then be tested for activity using in vitro or in vivo assays such as those described herein or any other suitable screening assay known in the art.

The polypeptides may comprise a consensus sequence which is discovered through rounds of experimentation. As used herein a "consensus" sequence is a single sequence which represents a collective population of sequences allowing for variability at one or more sites.

The nucleic acid agent, for example, may be a plasmid. Such a plasmid may comprise a nucleic acid sequence encoding such proteins, variants or isoforms thereof, although it is to be understood that other types of nucleic acid agents, such as recombinant viral vectors, may also be used for the purposes of the present invention. In one embodiment of the present invention, the nucleic acid (e.g., plasmid) encodes at least one variant or isoform.

As used herein, the term "plasmid" refers generally to circular double-stranded DNA, which is not bound to a chromosome. The DNA, for example, may be a chromosomal or episomal-derived plasmid. The plasmid of the present invention may optionally contain an initiator or promoter of transcription, and enhancer of transcription, a terminator of transcription, translational control sequences, and/or a discrete series of restriction-endonuclease recognition sites, located between the promoter and the terminator. In the plasmid, a polynucleotide insert of interest (e.g., one encoding an associated protein) should be operatively linked to an appropriate promoter. The promoter may be its native promoter or a host-derived promoter. The promoter and enhancer may also be a tissue-specific promoter, such as an adipocyte-specific promoter or other tissue-specific promoter. The promoter and enhancer may further be a regulatable, which may be turned off when the expression of the gene is no longer desired. Non-limiting examples of promoters/enhancers for use in the present invention include the actin promoter/enhancer and viral promoter/enhancers. Other suitable promoter/enhancers will be known to the skilled artisan.

As used herein, "therapeutic" is a generic term that includes both diagnosis and treatment. It will be appreciated that in these methods the "therapy" may be any therapy for treating a disease including, but not limited to, pharmaceutical compositions, gene therapy and biologic therapy such as the administering of antibodies and chemokines. Thus, the methods described herein may be used to evaluate a patient or subject before, during and after therapy, for example, to evaluate the reduction in disease state.

As used herein, "adjunctive therapy" is a treatment used in combination with a primary treatment to improve the effects of the primary treatment.

As used herein, "clinical outcome" refers to the health status of a patient following treatment for a disease or disorder or in the absence of treatment. Clinical outcomes include, but are not limited to, an increase in the length of time until death, a decrease in the length of time until death, an increase in the chance of survival, an increase in the risk of death, survival, disease-free survival, chronic disease, metastasis, advanced or aggressive disease, disease recurrence, death, and favorable or poor response to therapy.

As used herein, "decrease in survival" refers to a decrease in the length of time before death of a patient, or an increase in the risk of death for the patient.

As used herein, "patient" includes human and non-human animals. The preferred patient for treatment is a human. "Patient," "individual" and "subject" are used interchangeably herein.

As used herein, "preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

As used herein, "poor prognosis" generally refers to a decrease in survival, or in other words, an increase in risk of death or a decrease in the time until death. Poor prognosis can also refer to an increase in severity of the disease.

As used herein, "screening" refers to the process used to evaluate and identify candidate agents that affect such disease.

As used herein, "comprising, comprises and comprised of" are synonymous with "including", "includes" or "containing", "contains", and are inclusive or open-ended and do not exclude additional, non-recited members, elements or method steps. The terms "comprising", "comprises" and "comprised of" also include the term "consisting of".

As used herein, "about" generally refers to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

As used herein, "and/or," when used in a list of two or more items, means that any one of the listed items can be employed by itself or any combination of two or more of the listed items can be employed. For example, if a list is described as comprising group A, B, and/or C, the list can comprise A alone; B alone; C alone; A and B in combination; A and C in combination, B and C in combination; or A, B, and C in combination.

General Description

Described herein is a peptide-based mimetic(s) of the hGH site 1 helix (S1H) that corresponds to residues 36-51 of the full-length hGH. It is now believed that these peptides, which are direct sequence mimics of the hGH S1H, bind to the hGHR and competitively inhibit binding of the natural hormone.

It is now shown herein that S1H helical mimetics inhibits hGH-mediated tyrosine phosphorylation or activation of STAT5 in IM9 and SK-MEL cells.

It is also now shown herein that helical propensity has a significant influence on the ability for these peptides to inhibit hGHR signaling through STAT5 phosphorylation or any other hGH induced intracellular signaling pathway.

Also described herein is compound that inhibits hGH action. The compound is more efficacious, cheaper, and/or perhaps longer serum half-life than previous hGH compounds.

The compound is useful in treating patients with acromegaly and, in addition, in patients with hGH responsive cancers.

The compound is a small helical peptide that is amenable to manipulation such that the compound can be formulated into a long acting, orally active drug.

It is now believed that the peptide (S1H) is orally active (no injection) with a serum half-life adequate for one injection per day or perhaps less frequently.

S1H is useful for treatment of for acromegaly, all hGH responsive (i.e. hGHR expressing human) cancers, or any disorder where there is an increase in hGH levels or enhanced hGH action.

One non-limiting example is poorly controlled Type 1 diabetics where serum hGH levels are high and have been implicated in proliferative diabetic retinopathy and nephrology.

A hallmark of hGH action is rapid tyrosine phosphorylation of the STAT5(A and B) transcription factor protein following binding of hGH to hGHR and transactivation of hGHR associated JAK2. The phosphorylation event is rapid (minutes following hGH addition) and has been used as a readout of hGHR activation. Inhibitors of hGH action blocks hGH-hGHR mediated STAT5 tyrosine phosphorylation in many cells, including IM9, SK-MEL-28, mouse fibroblasts, and other cells which express hGHR.

S1H Peptide Inhibitor

The S1H peptide inhibitor robustly blocks tyrosine pSTAT5 levels following hGH stimulation, in a dose-dependent manner.

S1H is a short (16-amino acid) peptide that mimics a small, well-folded α-helix within site 1 of the hGH. This S1H peptide is a near-perfect sequence mimetic of the hGH between residues 36-51, a region within Site 1 of hGH that interacts with the hGHR. Based on x-ray crystallography data, this region is integral for favorable hGH:hGHR interactions.

S1H is a potent inhibitor of hGH:hGHR interactions. Further, described herein is the use of scanning alanine mutagenesis to determine which specific residues within the S1H sequence are important for helical propensity and inhibiting hGH signaling in live cells.

Examples

Certain embodiments of the present invention are defined in the Examples herein. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Methods

Reagents and Chemicals

Fmoc-PAL-AM resin, Fmoc-protected amino acids, and PyClock were each purchased from Novabiochem (Billerica, Mass.). Piperidine, N,N-diisopropylethylamine (DIEA), N-methyl-2-pyrrolidone (NMP), RIPA lysis buffer and Bradford reagent were purchased from Sigma-Aldrich (St. Louis, Mo.). Acetonitrile (ACN) was purchased from Alfa Aesar (Ward Hill, Mass.). Human malignant melanoma cell line, SK-MEL-28; human B lymphoblast cell line, IM9; EMEM, RPMI 1640 medium and fetal bovine serum (FBS) were purchased from American Type Culture Collection (ATCC; Manassas, Va.). The antibiotic-antimycotic, Halt protease and phosphatase inhibitor cocktail, and chemiluminescence detection reagents were purchased from Thermo Fisher Scientific (Waltham, Mass.). Recombinant hGH was purchased from Antibodies Online (Atlanta, Ga.). The monoclonal rabbit β-actin 4970S primary antibody and the rabbit pSTAT5 (Y694) 9351L primary antibodies were purchased from Cell Signaling Technology (Danvers, Mass.). All other materials were purchased from commercial sources and used without further purification.

Peptide Synthesis

All peptides were synthesized on PAL-AM resin using standard Fmoc solid phase peptide synthesis (SPPS) procedures. All reactions were performed on a 25 μmol scale in fritted glass reaction vessels to facilitate removal of reactants and starting materials. Amino acids and Fmoc deprotection were performed a microwave-accelerated reaction system (CEM, Matthews, N.C.) using software programs written in-house. Multiple rounds of washing using fresh NMP were performed between each coupling and deprotection reaction outlined herein. Amide bond formations were achieved by treating the deprotected resin with 5 equivalents (eq) of Fmoc-protected amino acid, 5 eq PyClock and 10 eq of DIEA in NMP. All equivalents are based on resin loading level. N-terminal Fmoc groups were removed by treating the peptide-resin with 25% (v/v) piperidine containing 0.1 M HOBt to minimize aspartimide formation. Iterative cycles of amino acid coupling and deprotections were repeated until peptides of desired sequence length were achieved. Following synthesis, the peptides were capped by treating the deprotected peptide-resin with 6% (v/v) acetic anhydride and 6% (v/v) 4-methylmorphine in NMP for 20 minutes at room temperature. This step was repeated and the capped peptide-resin was then washed thoroughly with NMP to remove any unreacted starting materials. Following washing, the resin was washed 5× with NMP, 5× with alternating volumes of NMP and dichloromethane and finally, 5× with dichloromethane. The resin was then allowed to dry under vacuum to remove the residual solvent.

Cleavage and Purification of Peptides

Following completion of the synthesis, dried resin-bound peptides were globally deprotected and cleaved from the resin by adding a cleavage cocktail of 88% (v/v) trifluoroacetic acid (TFA), 5% (v/v) water, 5% (v/v) phenol and 2% (v/v) triisopropylsilane. This reaction was then allowed to incubate for 30 minutes at 38° C. in the CEM microwave reactor. Following completion of the cleavage cycle, the peptides were precipitated in cold diethyl ether, pelleted by centrifugation, and resuspended in an appropriate volume of aqueous ACN. This solution was then frozen and lyophilized to remove residual solvent. Following lyophilization, crude peptide powders were resuspended in a suitable volume of aqueous ACN and purified across a semi-preparatory scale reversed-phase C18 column (Grace, 10 µm, 250×10 mm) using a ProStar® HPLC system (Agilent). Peptides were eluted over 30 minutes with a linear gradient of 15-45% solvent B (0.1% TFA in ACN) over solvent A (0.1% TFA in water). Absorbance spectra were monitored at 214 and 280 nm to distinguish peptide products. The identities of the eluted peptides were evaluated by mass spectrometry. Product peaks were combined, frozen and lyophilized twice. Peptide stocks were made by dissolving the purified peptide products in water and storing them at 4° C. All peptide concentrations were quantified using extinction coefficients calculated based on their respective primary sequences. Peptides were found to be stable for at least one year under these storage conditions.

General Characterization of Peptides by MS and Analytical HPLC

The identities of all peptides were confirmed using electrospray ionization mass spectrometry (ESI-MS). Masses were collected using a Thermo Scientific Q Exactive Plus Hybrid Quadrupole-Orbitrap® Mass Spectrometer in the m/z range of 500-2200. For analysis, peptides were dissolved in a suitable volume of 10% (v/v) ACN in water and directly injected to the ESI system. Data were processed using Xcalibur v3.0® (Thermo) and MagTran v1.00 deconvolution software (Amgen, Thousand Oaks, Calif.). Peptide purities were determined by analytical reversed-phase HPLC using an Agilent ProStar system. For analytical HPLC analysis, peptides were dissolved at a final concentration of 2.5 µM in water and injected across a reversed-phase C18 column (Grace, 5 µm, 50×2.1 mm). Peptides products were eluted over 20 minutes with a linear gradient of 5-95% solvent B (0.1% TFA in ACN) over solvent A (0.1% TFA in water). All peptides were purified to >95% as determined by product peak integration of analytical HPLC chromatograms. Analytical HPLC data were processed using OpenLab CDS ChemStation® Software (Agilent) version 1.06 and KaleidaGraph® version 4.5 (Synergy Software).

Structural Characterization of Peptide Products

The solution-phase structures of each peptide was evaluated by wavelength-dependent circular dichroism (CD). For analysis, stock peptides dissolved in water were diluted to a final concentration of 20 µM in phosphate buffered saline with or without 30% (v/v) 2,2,2-trifluoroethanol (TFE). These peptide solutions were then allowed to incubate for 10 minutes at 25° C. Wavelength scans were then performed on a Jasco J-715 spectropolarimeter from 260 to 190 nm at 25° C. Final spectra were generated from a background subtracted (buffer only) average of four scans. Data were processed using J-700® Software version 1.5 (Jasco) and KaleidaGraph® version 4.5 (Synergy Software).

Cell Culture and hGH Treatment

Human malignant melanoma cell lines—SK-MEL-28, SK-MEL-30, human lymphoblast IM9 cells, mouse fibroblast L cells were obtained from American Type Culture Collection (ATCC; Manassas, Va.). SK-MEL-28 were grown and maintained in EMEM media (ATCC), while IM9 and L cells were grown in RPMI-1640 (ATCC) and DMEM (ATCC) respectively, as indicated by ATCC protocols. Complete growth media was supplemented with 10% fetal bovine serum (FBS; ATCC) and 1× antibiotic-antimycotic (Thermo Fisher Scientific, Waltham, Mass.). Cells were grown at 37° C./5% CO2 in a humidified incubator. Media was replaced every 48 hours. No hGH was present in the media or added externally unless specifically mentioned. For hGH treatment of adherent cells, 12-16 hours after seeding the cells were serum-starved for 4 hours in serum free growth media and hGH (or PBS as control) was added at the mentioned concentrations (50 ng/mL=2.5 nM or other concentrations). For hGH treatment of suspension cells (IM9 cells), cells were pelleted by centrifuging at 140×g for 5 minutes at room temperature (RT), supernatant removed, and resuspended in serum-free media and starved for 4 hours and treated as described herein. Cells were subsequently incubated for 20 minutes for pSTAT5 detection unless mentioned otherwise. Recombinant hGH was purchased from Antibodies Online (Atlanta, Ga.). For treatment with candidate agonists (in absence of hGH), the same protocol was used. For treatment with candidate antagonists (in presence of hGH), the antagonists were added 1-2 minutes prior to hGH addition at RT. Pegvisomant (100 nM) was used as a positive control for hGHR-antagonism.

Protein Extraction

Total protein was collected following treatment for the corresponding time points.

Following treatment, cells were washed twice with ice-cold PBS and total protein was extracted from the cells using RIPA buffer (Sigma-Aldrich) (100 uL/million cells), mixed with 1.5× Halt protease and phosphatase inhibitor cocktail (Thermo Fisher Scientific), following the manufacturer's protocol. Briefly, chilled RIPA buffer was added and incubated for 5 minutes at 4° C. Then the cells were rapidly scraped with a sterile cell scraper for cell lysis. The cell lysate was sonicated briefly (1 min with 2-sec ON/1-sec OFF pulses) was clarified by centrifuging at 8,000×g for 10 minutes at 4° C. and the supernatant was collected and stored at −80° C. for subsequent use. Each sample was a pool of three replicates per experiment and each experiment was done three times.

Protein concentration was estimated using Bradford reagent (Sigma-Aldrich) and 1 mg/mL bovine serum albumin (BSA) as standard. Absorbance at 595 nm was measured using Spectramax250® (Molecular Devices, Sunnyvale, Calif.) and SoftmaxPro® v4.7.1 software.

Western Blotting (WB)

Western blotting was performed following established lab procedures. Briefly, cell lysates were separated by SDS-PAGE and transferred to activated PVDF membranes using wet-transfer method (20 V for 16 hours at 4° C.), blocked with 5% BSA in 1×TBS-T (Tris buffered saline, pH 7.2 with 0.1% Triton-X100) for 2 hours at 25° C., incubated with primary antibody (at specific dilutions given below) 16 hours at 4° C., and finally incubated with corresponding secondary antibodies (at specific dilutions given below) for 2 hours at 25° C. Membranes were then washed and treated with West Femto Chemiluminiscence® detection reagents (Thermo Fisher Scientific) and the chemiluminiscence signal was captured using a GelDoc® (Biorad) fluorescence reader. Densitometry analysis of the blots was done by measured band-intensity from the area-under-curve using ImageJ® software.

Primary antibodies at specific dilutions were used to detect the following human proteins: monoclonal Ab for pSTAT5B (Y699)+STAT5B (Y694) (rabbit, 1:5000, RnD Systems, cat #MAB41901), STAT5 (Rabbit, 1:100, CST #9358S), P(Y694)-STAT5 (polyclonal Rabbit, 1:1000, CST #9351), p44/42 MAPK (Erk1/2) (Rabbit, 1:2000, CST #91025), P-p44/42 MAPK (Erk1/2) (Rabbit, 1:3000, CST #4370P), Akt (Rabbit, 1:2000, CST #4685S), P-Akt (Rabbit, 1:1000, CST #4058S), P-Jak2 (Rabbit, 1:200, GeneTex #61122; Rabbit, 1:100, CST #8082), JAK2 (Mouse, 1:200, Sigma Aldrich #SAB4200483), mTOR (Rabbit, 1:1000, CST #2983), P-mTOR (Ser2448) (Rabbit, 1:2000, CST #5536), P-mTOR (Ser2481) (Rabbit, 1:2000, CST #2974), β-Actin (Goat, 1:3000, SCBT #sc1616), GAPDH (Goat, 1:3000, SCBT #sc20357).

Secondary antibodies used were anti-rabbit HRP-linked IgG (Donkey, 1:2000, CST #7074P2; 1:2000, GE #NA934), or anti-goat HRP-linked IgG (Donkey, 1:1000, SCBT #sc2020), or anti-mouse HRP-linked IgG (Rat, 1:1000, Antibodies Online #ABIN1589975).

ELISA

Samples used for western blot were parallelly quantified for pSTAT5 levels using InstantOne® ELISA kit (cat #85-86112-11; ThermoFisher) for detecting phosphorylated-STAT5A (Y694) and STAT5B (Y699), following manufacturer's instructions. Briefly, 50 μL of sample (1 mg/mL) was added to ELISA wells containing 50 μL antibody cocktail, and incubated at RT with 300 rpm shaking, for 2 hours. Wells were then thoroughly washed and binding was quantified by adding detection regent for 1 hour at RT with shaking at 300 rpm. Following incubation, stop reagent was added and the wells were read at 450 nm using a spectrophotometer. Experiments were performed in triplicate.

Statistical Analyses

Parametric and non-parametric statistical analyses were done using R software (ver3.0.2). The densitometry analyses, and ELISA results were compared by a paired students T-test and ANOVA was performed (using GraphPad Prism® software) to compare for significance ($p<0.05$ is considered significant).

Figure 2:
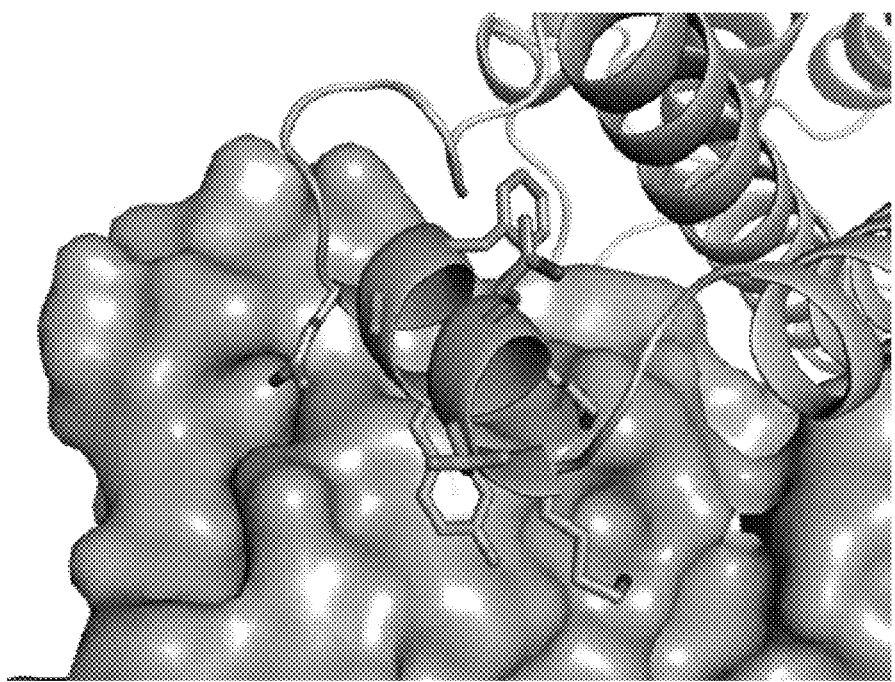
FIG. 2: Zoom of site 1 helix bound to the hGHR. Residues 36-51 are rendered as stick representations.

FIG. 1-2 show the three-dimensional crystal structure of the hGH bound to dimerized hGHR. FIG. 1 shows hGH (pink) is shown as a ribbon diagram bound to hGH (grey). The site 1 helix of hGH is colored purple. FIG. 2 shows zoom of site 1 helix bound to the hGHR. Residues 36-51 are rendered as stick representations.

Figure 3:
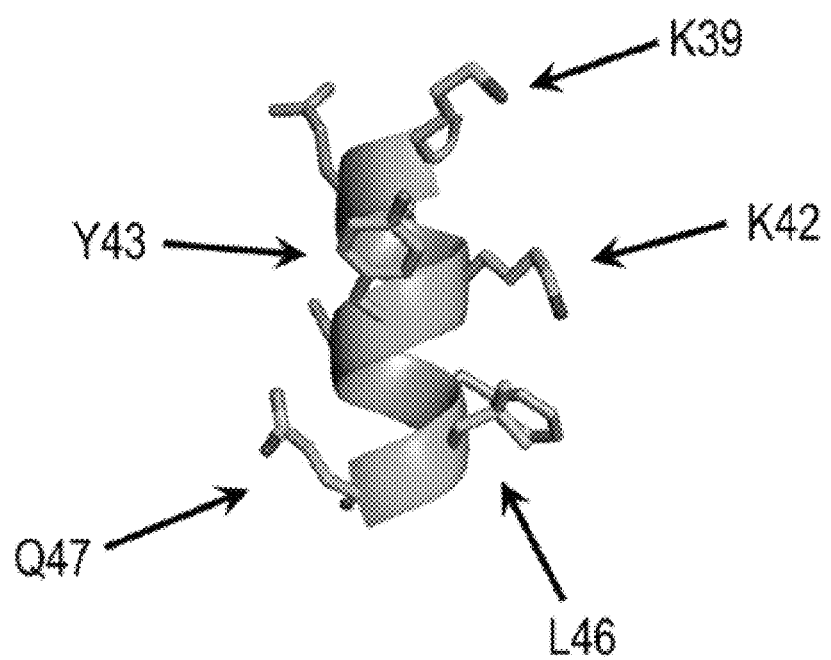
FIG. 3: Ribbon diagram of isolated S1H peptide helix of SEQ ID NO 1. Residues that make contact with the hGHR are colored green and indicated with arrows. Residues colored blue do not make contact with the hGHR. Color-coded primary sequence is shown underneath ribbon diagram.

FIG. 3 shows a ribbon diagram of S1H peptide helix. Residues that make contact with the hGHR are colored green and indicated with arrows. Residues colored blue do not make contact with the hGHR. Color-coded primary sequence is shown underneath ribbon diagram.

Figure 4:
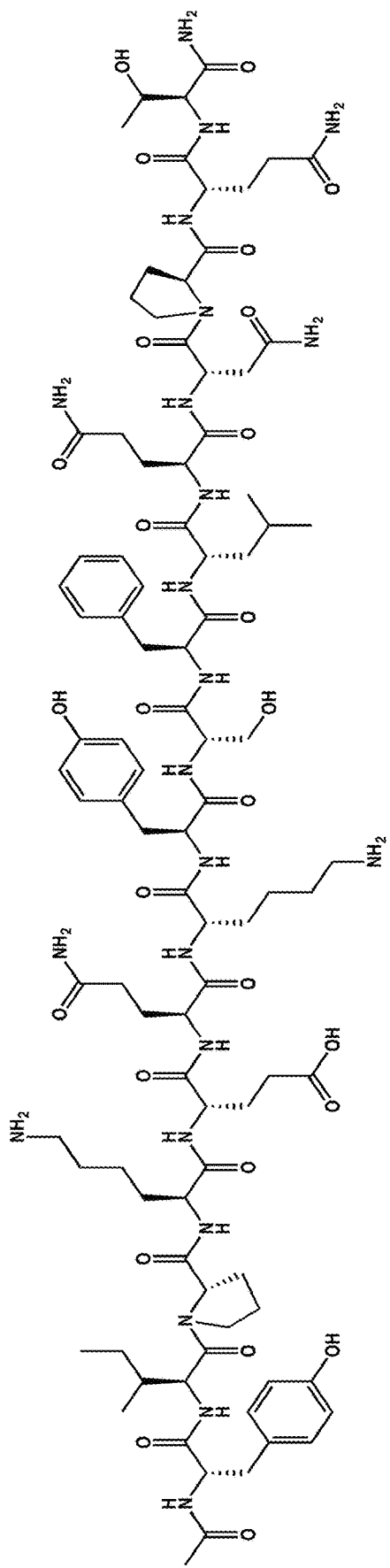
FIG. 4: Full chemical structure of S1H (36-51) peptide.

FIG. 4 is the full chemical structure of S1H (36-51) peptide. N-terminus is shown capped with an acetyl group; C-terminus is an amide.

Figure 5:
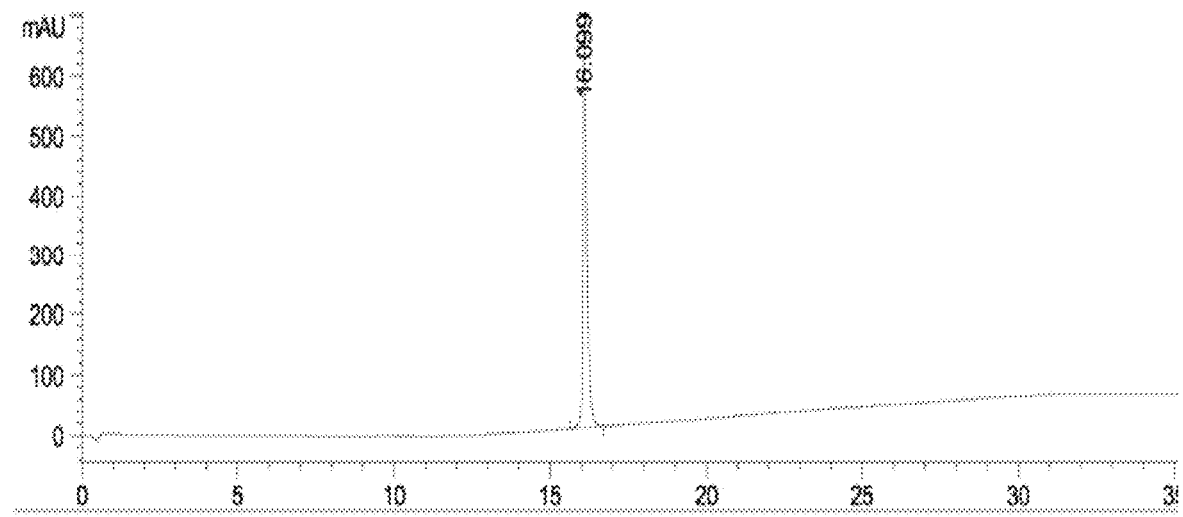
FIG. 5: Representative analytical HPLC chromatogram of purified peptide S1H.

FIG. 5 shows a representative analytical HPLC chromatogram of peptide purified S1H. Retention time (min) is shown above the trace. Spectra was monitored at 214 nm. mAU: milli-absorbance units.

Figure 6:
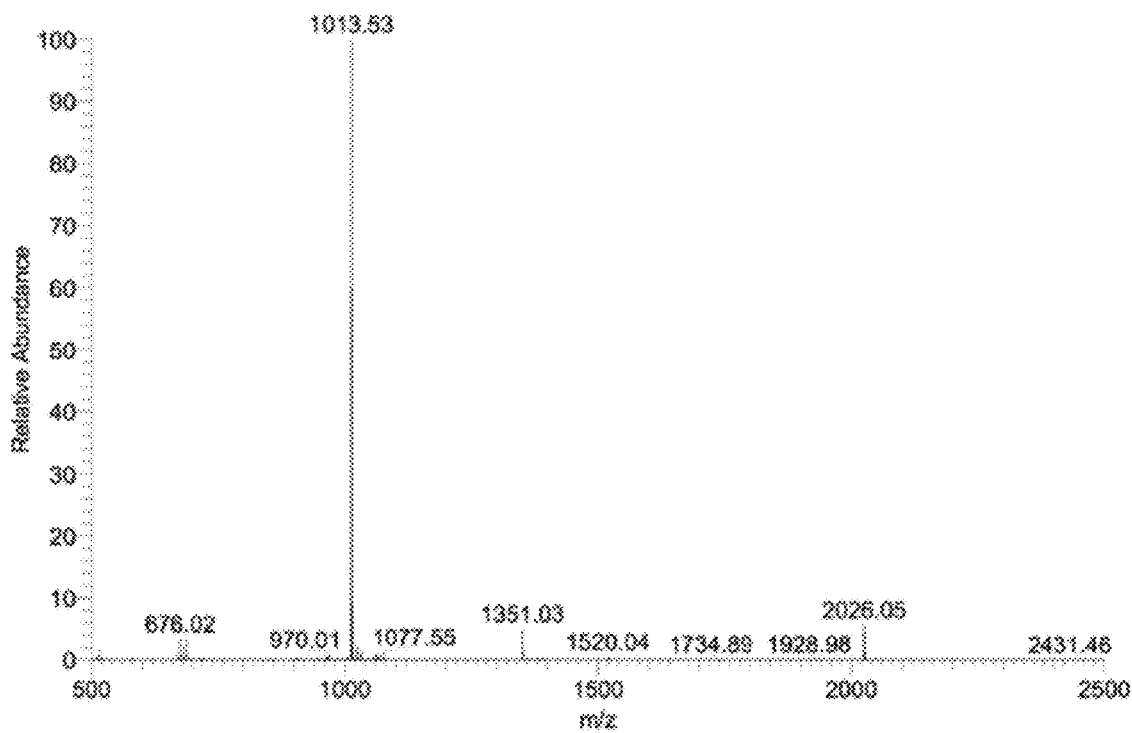
FIG. 6: Representative mass spectrum of S1H peptide. Calculated mass: 2025.04 m/z; Observed mass: 2026.46 m/z. Large peak corresponds to $(M+2H^+)/2$ mass: 1013.53 $(m+2H^+)/2z$.

FIG. 6 shows a representative mass spectrum of S1H peptide. Calculated mass:

2025.04 m/z; Observed mass: 2026.46 m/z. Large peak corresponds to $(M+2H^+)/2$ mass: 1013.53 $(m+2H^+)/2z$.

Figure 7:
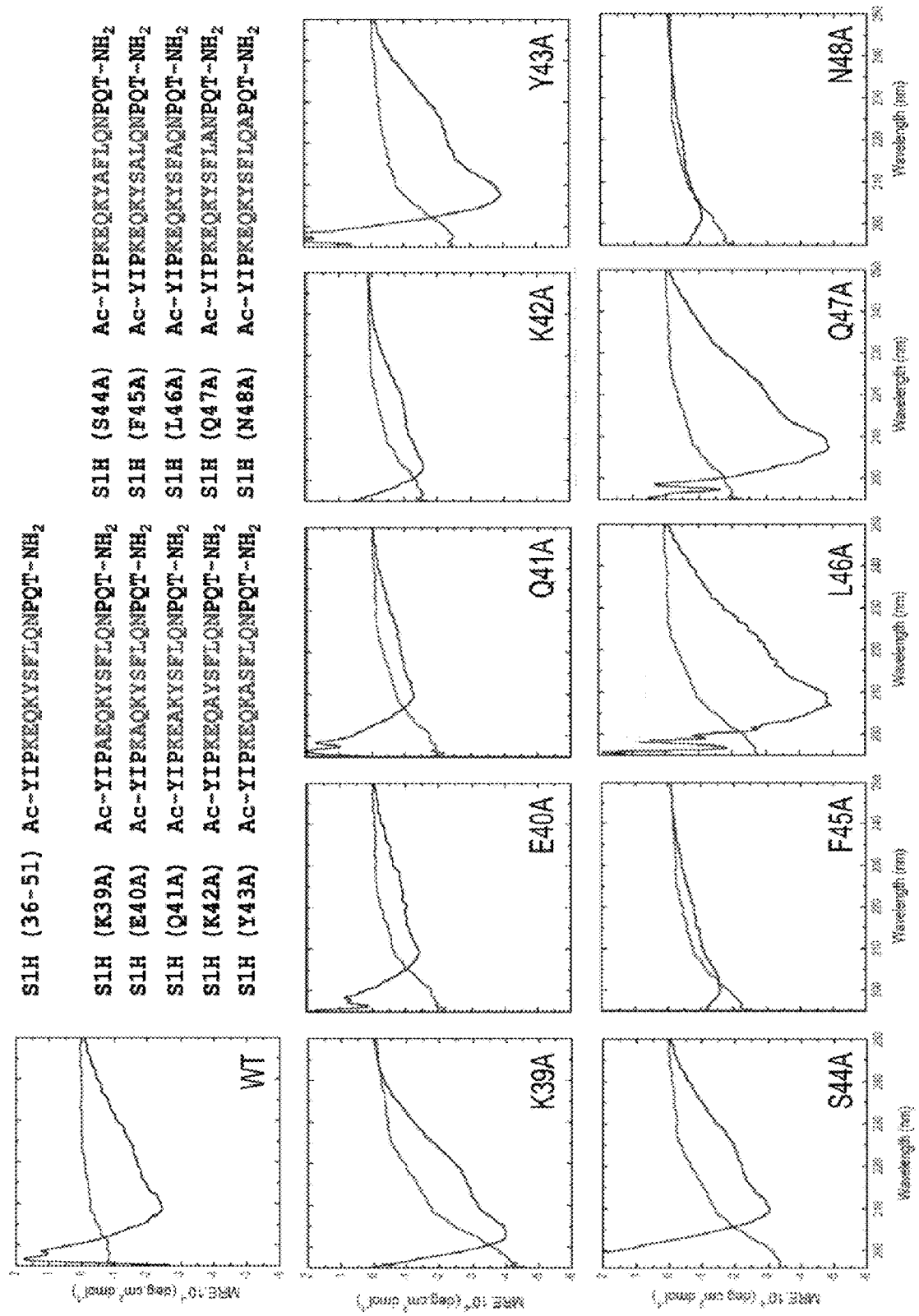
FIG. 7: Wavelength-dependent circular dichroism spectra of S1H peptide and scanning alanine library. Red spectra show peptides in PBS only; blue spectra represent peptides in PBS supplemented with 30% TFE. Primary sequences of each peptide are shown above the CD spectra. Left column showing SEQ ID NOs: 1-6; right column showing SEQ ID NO:7-11.

FIG. 7 shows the wavelength-dependent circular dichroism spectra of S1H peptide [SEQ ID NO:1] and scanning alanine library for SEQ. ID Nos: 2-11. Red spectra show peptides in PBS only; blue spectra represent peptides in PBS supplemented with 30% TFE. All spectra were collected at 25° C. Primary sequences of each peptide are shown above the CD spectra.

FIG. 8 is a table showing sequences and mass data for peptides described herein.

Figure 9:
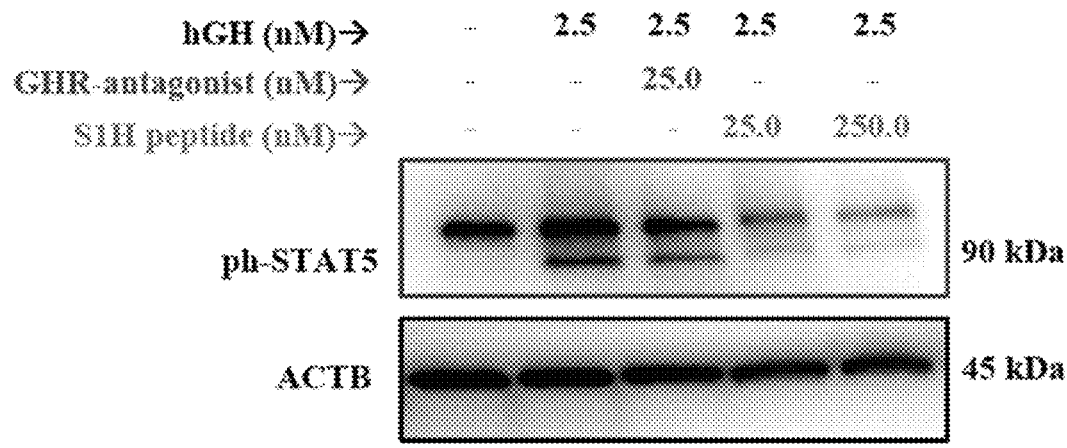
FIG. 9: Inhibitor peptide (S1H) downregulates hGH mediated STAT5 phosphorylation in SK-MEL-28 human melanoma cells

FIG. 9 Western blot showing the inhibitor peptide (S1H) downregulates hGH mediated STAT5 phosphorylation in SK-MEL-28 human melanoma cells. Human SK-MEL-28 melanoma cells were co-treated with 2.5 nM recombinant hGH with or without peptide inhibitor at 25 and 250 nM, for 20 minutes and assayed for pSTAT5 levels. β-actin (ACTB) was used as a loading control.

Figure 10:
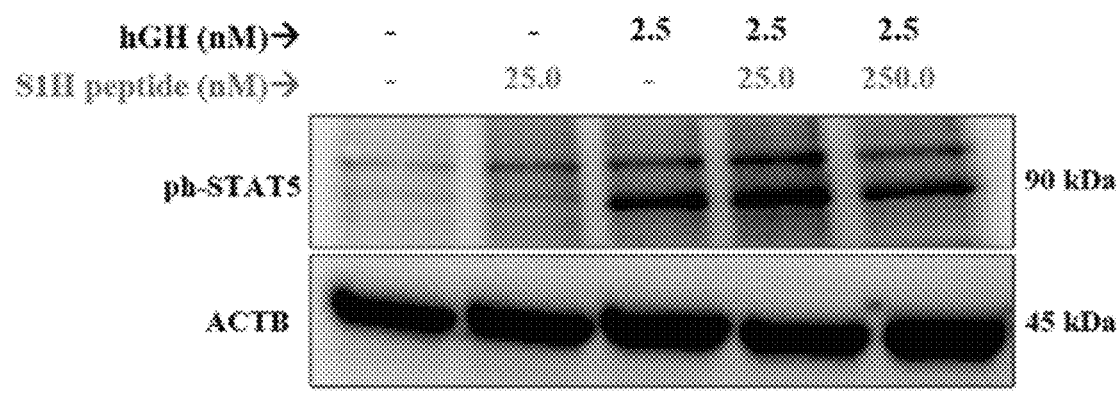
FIG. 10: Inhibitor peptide (S1H) downregulates hGH mediated STAT5 phosphorylation in IM9 human lymphoblast cells.

FIG. 10 Western blot showing that inhibitor peptide (S1H) downregulates hGH mediated STAT5 phosphorylation in IM9 human lymphoblast cells. Human IM9 cells were co-treated with 2.5 nM recombinant hGH with or without peptide inhibitor at 25 and 250 nM, for 20 minutes and assayed for phospho-STAT5 levels. β-actin (ACTB) was used as a loading control.

Figure 11:
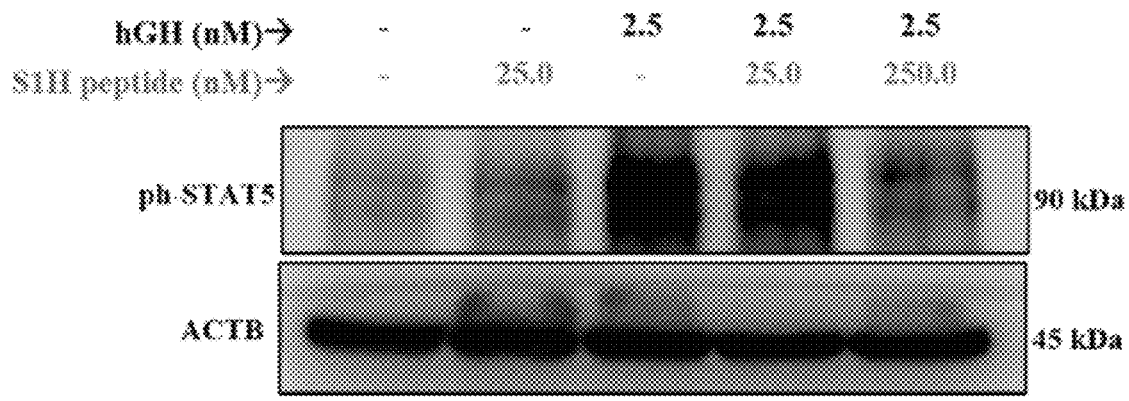
FIG. 11: Inhibitor peptide (S1H) downregulates hGH mediated STAT5 phosphorylation in L mouse fibroblasts cells.

FIG. 11 Western blot showing that inhibitor peptide (S1H) downregulates hGH mediated STAT5 phosphorylation in L mouse fibroblasts cells. The cells were co-treated with 2.5 nM recombinant hGH with or without peptide inhibitor at 25 and 250 nM, for 20 minutes and assayed for phospho-STAT5 levels. β-actin (ACTB) was estimated as a loading control.

Figure 12A:
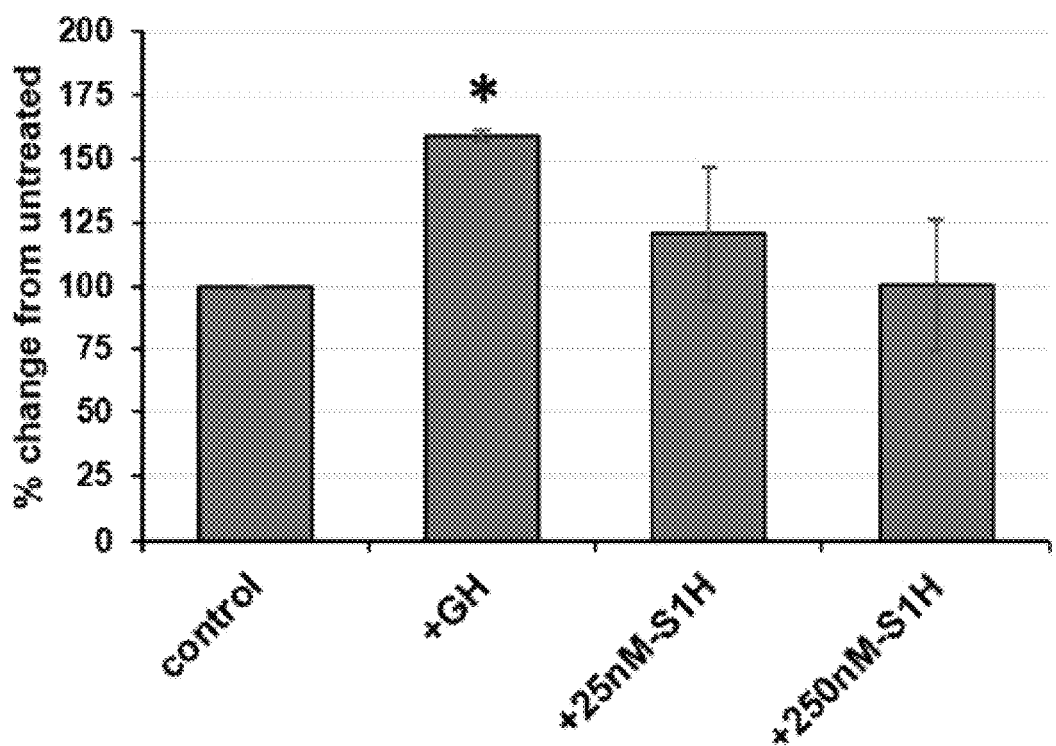
FIG. 12A: ELISA analyses of agonist properties of peptide (S1H) in upregulating hGH mediated STAT5 phosphorylation in SK-MEL-28 human melanoma cells.
Figure 12B:
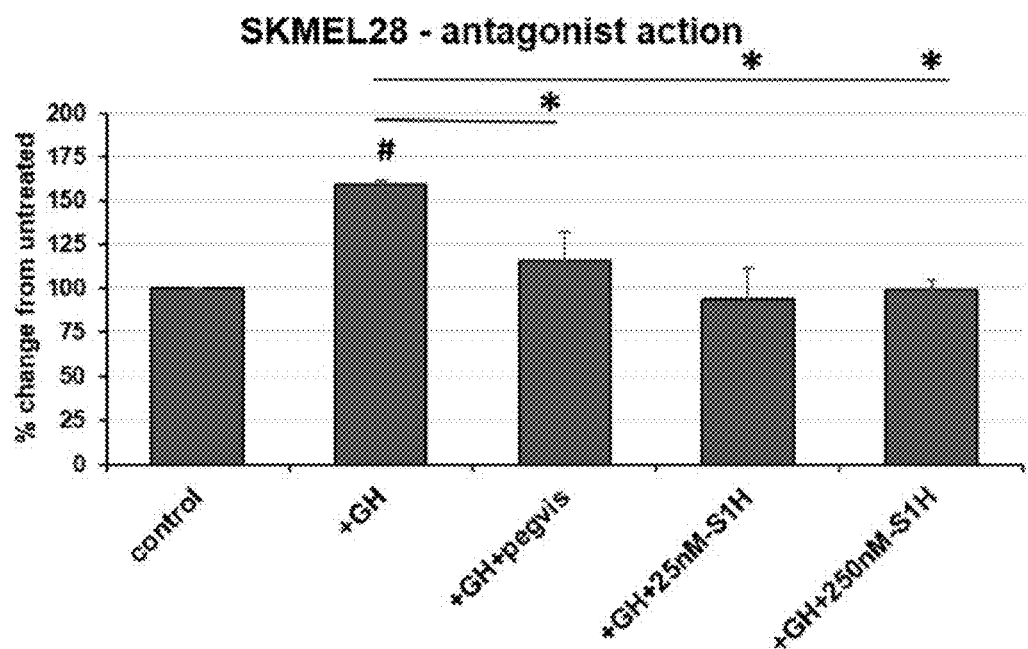
FIG. 12B: ELISA analyses of antagonist properties of inhibitor peptide (S1H) in downregulating hGH mediated STAT5 phosphorylation in SK-MEL-28 human melanoma cells.

FIG. 12A shows ELISA analyses of agonist properties of peptide (S1H) in upregulating hGH mediated STAT5 phosphorylation in SK-MEL-28 human melanoma cells. FIG. 12B shows ELISA analyses of antagonist properties of inhibitor peptide (S1H) in downregulating hGH mediated STAT5 phosphorylation in SK-MEL-28 human melanoma cells. The cells were co-treated with 2.5 nM recombinant hGH with or without peptide inhibitor at 25 and 250 nM, for 20 minutes and assayed for pSTAT5 levels using monoclonal antibody to STAT5A and STAT5B using sandwich-ELISA (ThermoFisher). [pegvis=pegvisomant]; [GH=human growth hormone].

Figure 13:
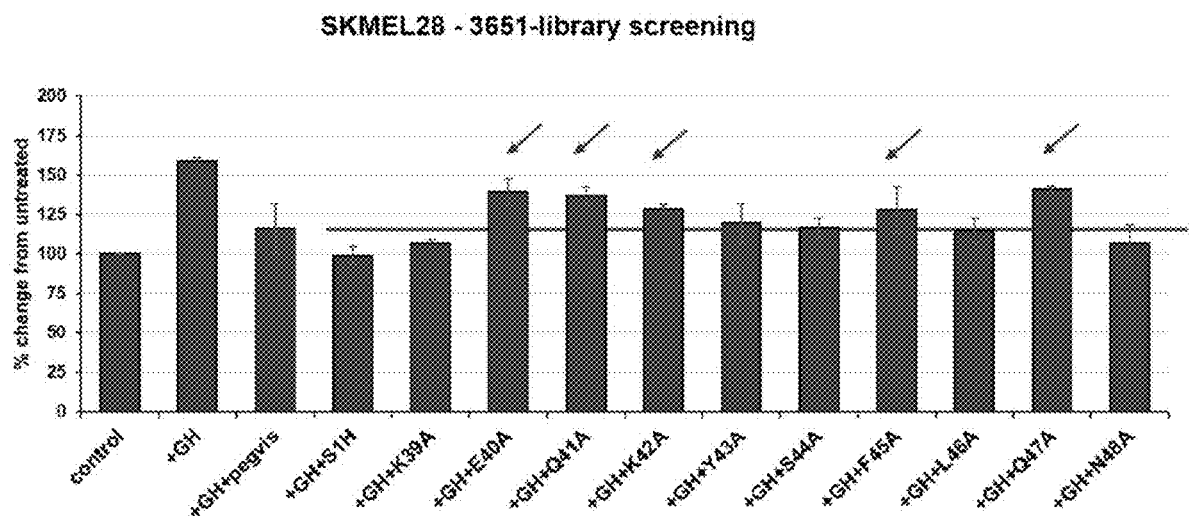
FIG. 13: ELISA analyses of antagonist properties of inhibitor peptide (S1H) and alanine mutants of the same in downregulating hGH mediated STAT5 phosphorylation in SK-MEL-28 human melanoma cells. Arrows indicate peptide treatments that show reduced antagonist activity. Horizontal line indicates level of inhibition by the commercially available hGHR antagonist Pegvisomant®.

FIG. 13 shows the ELISA analyses of antagonist properties of inhibitor peptide (S1H) and alanine mutants of the same in downregulating hGH mediated STAT5 phosphorylation in SK-Mel-28 human melanoma cells. The cells were co-treated with 2.5 nM recombinant hGH with or without peptide inhibitors at 250 nM, for 20 minutes and assayed for pSTAT5 levels using monoclonal antibody to pSTAT5A and pSTAT5B using sandwich-ELISA (ThermoFisher). Arrows indicate peptide treatments that show reduced antagonist activity. Horizontal line indicates level of inhibition by the commercially available hGHR antagonist Pegvisomant®. [GH=human growth hormone].

Examples of Growth Hormone Disorders Treatable with S1H

Diseases that may be treated by the methods of the invention are diseases characterized by one or more of the following criteria: elevated levels of hGH production, elevated levels of serum hGH, elevated levels of hGHR production, and elevated cellular response of hGHRs to hGH.

The term "elevated" as used herein is used with respect to the normal levels of hGH production, hGHR production, or hGH-mediated cellular response in a tissue (or tissues) of a diseased person (or animal) as compared to level in a normal individual. Diseases that may be treated by the methods of the invention include, but are not limited to, acromegaly, gigantism, cancer, diabetes, vascular eye diseases (diabetic retinopathy, retinopathy of prematurity, age-related macular degeneration, retinopathy of sickle-cell anemia, (etc.) as well as nephropathy.

Cancers that may be treated by the subject method include, but are not limited to, cancers comprising tumor cells that express hGHRs. Cancers that may be treated by the methods of the invention include, but are not limited to:

Cardiac: sarcoma (angiosarcoma, fibrosarcoma, rhabdomyosarcoma, liposarcoma), myxoma, rhabdomyoma, fibroma, lipoma and teratoma.

Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma.

Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma).

Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma).

Liver: hepatoma (hepatocellular carcinoma), cholangiocarcinoma, hepatoblastoma, angiosarcoma, hepatocellular adenoma, hemangioma.

Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor, chordoma, osteochronfroma (osteocartilaginous exostoses), benign chondroma, chondroblastoma, chondromyxofibroma, osteoid osteoma and giant cell tumors.

Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiforme, oligodendroglioma, schwannoma, retinoblastoma, congenital tumors), spinal cord (neurofibroma, meningioma, glioma, sarcoma).

Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, endometrioid tumors, celioblastoma, clear cell carcinoma, unclassified carcinoma], granulosathecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma [embryonal rhabdomyosarcoma], fallopian tubes (carcinoma).

Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma].

Skin: malignant melanoma, basal cell carcinoma, squamous cell carcinoma, Karposi's sarcoma, moles, dysplastic nevi, lipoma, angioma, dermatofibroma, keloids, psoriasis.

Adrenal glands: neuroblastoma.

Other cancer: breast cancers, colon/colorectal cancers, thyroid cancers.

Pharmaceutical Compositions

A pharmaceutical composition as described herein may be formulated with any pharmaceutically acceptable excipients, diluents, or carriers. A composition disclosed herein may comprise different types of carriers depending on whether it is to be administered in solid, liquid, or aerosol form, and whether it needs to be sterile for such routes of administration as injection. Compositions disclosed herein can be administered in a suitable manner, including, but not limited to topically (i.e., transdermal), subcutaneously, nasally, orally, aerosols, by localized perfusion bathing target cells directly, via a lavage, in creams, in lipid compositions (e.g., liposomes), formulated as elixirs or solutions for convenient topical administration, formulated as sustained release dosage forms, or by other method or any combination of the forgoing as would be known to one of ordinary skill in the art (see, for example, Remington's Pharmaceutical Sciences, 2015, incorporated herein by reference).

The compositions provided herein are useful for treating animals, such as humans. A method of treating a human patient according to the present disclosure includes the administration of a composition, as described herein.

The phrases "pharmaceutical" or "pharmacologically acceptable" refer to molecular entities and compositions that produce no adverse, allergic, or other untoward reaction when administered to an animal, such as, for example, a human. A carrier or diluent may be a solid, semi-solid, or liquid material which serves as a vehicle, excipient, or medium for the active therapeutic substance. Some examples of the diluents or carriers which may be employed in the pharmaceutical compositions of the present disclosure are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of theobroma, arachis oil, alginates, tragacanth, gelatin, syrup, methyl cellulose, polyoxyethylene sorbitan monolaurate, ethyl lactate, methyl and propyl hydroxybenzoate, sorbitan trioleate, sorbitan sesquioleate and oleyl alcohol, and propellants such as trichloromonofluoromethane, dichlorodifluoromethane, and dichlorotetrafluoroethane.

The phrase "chemotherapeutic agent" refers to a therapeutic agent known to be used in treating a subject that has been diagnosed with cancer Some examples of general classes of chemotherapeutic agents of the present disclosure include alkylating agents, anthracyclines, cytoskeletal disruptors, epothilones, histone deacetylase inhibitors, inhibitors of topoisomerase I and II, kinase inhibitors, nucleotide analogs and precursor analogs, peptide antibiotics, platinum-based agents, retinoids, and vina alkaloids and derivatives, and a variety of antibodies specific antigens on cancer cells. Of these general classes, specific examples include but are not limited to doxorubicin (Adriamycin), sorafenib tosylate, cisplatin, paclitaxel, gemcitabine, vemurafenib, dabrafenib, linsitinib, crizotinib, and cabozantinib.

Solutions of the compositions disclosed herein as free bases or pharmacologically acceptable salts may be prepared in water suitably mixed with a surfactant, such as hydroxypropylcellulose. Dispersions may also be prepared in glycerol, liquid polyethylene glycols, and mixtures thereof, and in oils. Under ordinary conditions of storage and use, these preparations contain a preservative to prevent the growth of microorganisms. The pharmaceutical forms suitable for use include sterile aqueous solutions or dispersions and sterile powders for the extemporaneous preparation of sterile solutions or dispersions. In certain cases, the form should be sterile and should be fluid to the extent that easy injectability exists. It should be stable under the conditions of manufacture and storage and may optionally be preserved against the contaminating action of microorganisms, such as bacteria and fungi. The carrier can be a solvent or dispersion medium containing, for example, water, ethanol, a polyol (i.e., glycerol, propylene glycol, and liquid polyethylene glycol, and the like), suitable mixtures thereof, and/or vegetable oils. The prevention of the action of microorganisms can be brought about by various antibacterial and antifungal agents, for example, parabens, chlorobutanol, phenol, sorbic acid, thimerosal, and the like. In many cases, it may be preferable to include isotonic agents, such as, but not limited to, sugars or sodium chloride.

Pharmaceutical compositions for topical administration may include the compositions formulated for a medicated application such as an ointment, paste, cream, or powder. Ointments include all oleaginous, adsorption, emulsion, and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and luarocapram. Possible bases for compositions for topical application include polyethylene glycol, lanolin, cold cream, and petrolatum as well as any other suitable absorption, emulsion, or water-soluble ointment base. Topical preparations may also include emulsifiers, gelling agents, and antimicrobial preservatives as necessary to preserve the composition and provide for a homogenous mixture. Transdermal administration of the compositions may also comprise the use of a "patch." For example, the patch may supply one or more compositions at a predetermined rate and in a continuous manner over a fixed time-period.

It is further envisioned the compositions disclosed herein may be delivered via an aerosol. The term aerosol refers to a colloidal system of finely divided solid or liquid particles dispersed in a liquefied or pressurized gas propellant. The typical aerosol comprises a suspension of active ingredients in liquid propellant or a mixture of liquid propellant and a suitable solvent. Suitable propellants include hydrocarbons and hydrocarbon ethers. Suitable containers can vary according to the pressure requirements of the propellant. Administration of the aerosol can vary according to subject's age, weight, and the severity and response of the symptoms.

Dosage

The actual dosage amount of a composition disclosed herein administered to an animal or human patient can be determined by physical and physiological factors such as body weight, severity of condition, the type of disease being treated, previous or concurrent therapeutic interventions, idiopathy of the patient, and the route of administration. Depending upon the dosage and the route of administration, the number of administrations of a preferred dosage and/or an effective amount may vary according to the response of the subject. The compounds of the present disclosure are generally effective over a wide dosage range. The practitioner responsible for administration can, in any event, determine the concentration of active ingredient(s) in a composition and appropriate dose(s) for the individual subject.

Naturally, the amount of active compound(s) in each therapeutically useful composition may be prepared in such a way that a suitable dosage can be obtained in any given unit dose of the compound. Factors such as solubility, bioavailability, biological half-life, route of administration, product shelf life, as well as other pharmacological considerations can be contemplated by those preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above. The dosages can depend on many factors, and can in any event be determined by a suitable practitioner. Therefore, the dosages described herein are not intended to be limiting.

In some embodiments, the compositions further include an additional active ingredient. The preparation of a pharmaceutical composition that contains at least one compound or additional active ingredient can be known to those of skill in the art in light of the present disclosure, as exemplified by Remington's Pharmaceutical Sciences, 2003, incorporated herein by reference. Moreover, for animal (e.g., human) administration, it can be understood that preparations should meet sterility, pyrogenicity, and general safety and purity standards as required by the FDA Office of Biological Standards.

Packaging of the Composition

After formulation, the composition is packaged in a manner suitable for delivery and use by an end user. In one embodiment, the composition is placed into an appropriate dispenser and shipped to the end user. Examples of final container may include a pump bottle, squeeze bottle, jar, tube, capsule or vial.

The compositions and methods described herein can be embodied as parts of a kit or kits. A non-limiting example of such a kit comprises the ingredients for preparing a composition, where the containers may or may not be present in a combined configuration. In certain embodiments, the kits further comprise a means for administering the composition, such as a topical applicator, or a syringe. The kits may further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive, CD-ROM, or diskette. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

What is claimed is:

1. A synthetic polypeptide consisting of amino acid sequence (SEQ ID NO: 13) Tyr-Ile-Pro-$X_4$-Glu-Gln-Lys-$X_8$-$X_9$-Phe-$X_{11}$-Gln-$X_{13}$-Pro-Gln-Thr;
   wherein, independently from each other:
   $X_4$ is Lys or Ala or other conservative polar amino acid substitution;
   $X_5$ is Tyr or Ala or other conservative hydrophobic amino acid substitution,
   $X_6$ is Ser or Ala or other conservative polar non-charged amino acid substitution,
   $X_{11}$ is Leu or Ala or other conservative hydrophobic amino acid substitution, and,
   $X_{13}$ is Asn or Ala or other conservative polar non-charged amino acid substitution;
   wherein the synthetic polypeptide is capped with an acyl group, acetyl group or fluorophore, and an amide at the C-terminus;
   wherein the synthetic polypeptide is a cyclic peptide having intramolecular cross-linking between amino acid side chains; and,
   wherein the synthetic polypeptide mimics a folded a-helix within human growth hormone (hGH); and inhibits hGH binding to human growth hormone receptor (hGHR), and inhibits intracellular signaling cascades that are controlled by hGH.

2. The synthetic polypeptide of claim 1, consisting of amino acid sequence of S1H [SEQ ID NO: 1]: Tyr Ile Pro Lys Glu Gln Lys Tyr Ser Phe Leu Gln Asn Pro Gln Thr.

3. A human growth hormone (hGH) inhibiting composition comprising at least one synthetic polypeptide of claim 1.

4. The composition of claim 3, wherein the synthetic polypeptide is a sequence mimetic of the human growth Hormone (hGH) between residues 36-51 which is a region within Site 1 of the hGH that interacts with the hGHR.

5. The composition of claim 3, wherein the synthetic polypeptide has [SEQ ID NO: 1] Tyr Ile Pro Lys Glu Gln Lys Tyr Ser Phe Leu Gln Asn Pro Gln Thr.

6. The composition of claim 3, wherein the composition further comprises a pharmaceutically acceptable excipient, diluent, adjuvant, or carrier.

7. A synthetic polypeptide consisting of amino acid sequence (SEQ ID NO: 14)
   Tyr-Ile-Pro-$X_4$-$X_5$-$X_6$-$X_7$-$X_8$-$X_9$-$X_{10}$-$X_{11}$-$X_{12}$-$X_{13}$-Pro-Gln-Thr;
   wherein, independently from each other:
   $X_4$ is Lys or Ala,
   $X_5$ is Glu or Ala,
   $X_6$ is Gln or Ala,
   $X_7$ is Lys or Ala,
   $X_8$ is Tyr or Ala,
   $X_9$ is Ser or Ala,
   $X_{10}$ is Phe or Ala,
   $X_{11}$ is Leu or Ala,
   $X_{12}$ is Gln or Ala,
   $X_{13}$ is Asn or Ala;
   wherein the synthetic polypeptide is a cyclic peptide having intramolecular cross-linking between amino acid side chains; and,
   wherein the synthetic polypeptide mimics a folded a-helix within human growth hormone (hGH) and inhibits expression of hGH.

8. The polypeptide of claim 1, having amino acid sequence of SEQ ID NO: 2: Tyr Ile Pro Ala Glu Gln Lys Tyr Ser Phe Leu Gln Asn Pro Gln Thr.

9. The polypeptide of claim 1, having amino acid sequence of SEQ ID NO: 3: Tyr Ile Pro Lys Ala Gln Lys Tyr Ser Phe Leu Gln Asn Pro Gln Thr.

10. The polypeptide of claim 1, having amino acid sequence of SEQ ID NO: 4: Tyr Ile Pro Lys Glu Ala Lys Tyr Ser Phe Leu Gln Asn Pro Gln Thr.

11. The polypeptide of claim 1, having amino acid sequence of SEQ ID NO: 5: Tyr Ile Pro Lys Glu Gln Ala Tyr Ser Phe Leu Gln Asn Pro Gln Thr.

12. The polypeptide of claim 1, having amino acid sequence of SEQ ID NO: 6: Tyr Ile Pro Lys Glu Gln Lys Ala Ser Phe Leu Gln Asn Pro Gln Thr.

13. The polypeptide of claim 1, having amino acid sequence of [SEQ ID NO: 7] Tyr Ile Pro Lys Glu Gln Lys Tyr Ala Phe Leu Gln Asn Pro Gln Thr.

14. The polypeptide of claim 1, having amino acid sequence of [SEQ ID NO: 8] Tyr Ile Pro Lys Glu Gln Lys Tyr Ser Ala Leu Gln Asn Pro Gln Thr.

15. The polypeptide of claim 1, having amino acid sequence of [SEQ ID NO: 9] Tyr Ile Pro Lys Glu Gln Lys Tyr Ser Phe Ala Gln Asn Pro Gln Thr.

16. The polypeptide of claim 1, having amino acid sequence of [SEQ ID NO: 10] Tyr Ile Pro Lys Glu Gln Lys Tyr Ser Phe Leu Ala Asn Pro Gln Thr.

17. The polypeptide of claim 1, having amino acid sequence of [SEQ ID NO: 11] Tyr Ile Pro Lys Glu Gln Lys Tyr Ser Phe Leu Gln Ala Pro Gln Thr.

* * * * *

```
                        SEQUENCE LISTING

<160> NUMBER OF SEQ ID NOS: 14

<210> SEQ ID NO 1
    <211> LENGTH: 16
    <212> TYPE: PRT
    <213> ORGANISM: Artificial Sequence
    <220> FEATURE:
    <223> OTHER INFORMATION: Description of Artificial Sequence: Synthetic
          peptide

<400> SEQUENCE: 1

Tyr Ile Pro Lys Glu Gln Lys Tyr Ser Phe Leu Gln Asn Pro Gln Thr
    1               5                   10                  15

<210> SEQ ID NO 2
    <211> LENGTH: 16
    <212> TYPE: PRT
    <213> ORGANISM: Artificial Sequence
    <220> FEATURE:
    <223> OTHER INFORMATION: Description of Artificial Sequence: Synthetic
          peptide

<400> SEQUENCE: 2

Tyr Ile Pro Ala Glu Gln Lys Tyr Ser Phe Leu Gln Asn Pro Gln Thr
    1               5                   10                  15

<210> SEQ ID NO 3
    <211> LENGTH: 16
    <212> TYPE: PRT
    <213> ORGANISM: Artificial Sequence
    <220> FEATURE:
    <223> OTHER INFORMATION: Description of Artificial Sequence: Synthetic
          peptide

<400> SEQUENCE: 3

Tyr Ile Pro Lys Ala Gln Lys Tyr Ser Phe Leu Gln Asn Pro Gln Thr
    1               5                   10                  15

<210> SEQ ID NO 4
    <211> LENGTH: 16
    <212> TYPE: PRT
    <213> ORGANISM: Artificial Sequence
    <220> FEATURE:
    <223> OTHER INFORMATION: Description of Artificial Sequence: Synthetic
          peptide

<400> SEQUENCE: 4

Tyr Ile Pro Lys Glu Ala Lys Tyr Ser Phe Leu Gln Asn Pro Gln Thr
    1               5                   10                  15
```

```
<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Tyr Ile Pro Lys Glu Gln Ala Tyr Ser Phe Leu Gln Asn Pro Gln Thr
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Tyr Ile Pro Lys Glu Gln Lys Ala Ser Phe Leu Gln Asn Pro Gln Thr
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Tyr Ile Pro Lys Glu Gln Lys Tyr Ala Phe Leu Gln Asn Pro Gln Thr
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Tyr Ile Pro Lys Glu Gln Lys Tyr Ser Ala Leu Gln Asn Pro Gln Thr
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Tyr Ile Pro Lys Glu Gln Lys Tyr Ser Phe Ala Gln Asn Pro Gln Thr
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 10

Tyr Ile Pro Lys Glu Gln Lys Tyr Ser Phe Leu Ala Asn Pro Gln Thr
1               5                   10                  15

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Tyr Ile Pro Lys Glu Gln Lys Tyr Ser Phe Leu Gln Ala Pro Gln Thr
1               5                   10                  15

<210> SEQ ID NO 12
<211> LENGTH: 192
<212> TYPE: PRT
<213> ORGANISM: Homo sapiens

<400> SEQUENCE: 12

Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
                20                  25                  30

Glu Glu Ala Tyr Ile Pro Lys Glu Gln Lys Tyr Ser Phe Leu Gln Asn
            35                  40                  45

Pro Gln Thr Ser Leu Cys Phe Ser Glu Ser Ile Pro Thr Pro Ser Asn
        50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                85                  90                  95

Val Phe Ala Asn Ser Leu Val Tyr Gly Ala Ser Asp Ser Asn Val Tyr
            100                 105                 110

Asp Leu Leu Lys Asp Leu Glu Glu Gly Ile Gln Thr Leu Met Gly Arg
        115                 120                 125

Leu Glu Asp Gly Ser Pro Arg Thr Gly Gln Ile Phe Lys Gln Thr Tyr
    130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                165                 170                 175

Phe Leu Arg Ile Val Gln Cys Arg Ser Val Glu Gly Ser Cys Gly Phe
            180                 185                 190

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Lys or Ala or other conservative polar amino
      acid substitution
<220> FEATURE:
<221> NAME/KEY: MOD_RES
<222> LOCATION: (8)..(8)
```

```
<223> OTHER INFORMATION: Tyr or Ala or other conservative hydrophobic
      amino acid substitution
<220> FEATURE:
<221> NAME/KEY: MOD_RES
<222> LOCATION: (9)..(9)
<223> OTHER INFORMATION: Ser or Ala or other conservative polar
      non-charged amino acid substitution
<220> FEATURE:
<221> NAME/KEY: MOD_RES
<222> LOCATION: (11)..(11)
<223> OTHER INFORMATION: Leu or Ala or other conservative hydrophobic
      amino acid substitution
<220> FEATURE:
<221> NAME/KEY: MOD_RES
<222> LOCATION: (13)..(13)
<223> OTHER INFORMATION: Asn or Ala or other conservative polar
      non-charged amino acid substitution

<400> SEQUENCE: 13

Tyr Ile Pro Xaa Glu Gln Lys Xaa Xaa Phe Xaa Gln Xaa Pro Gln Thr
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Lys or Ala
<220> FEATURE:
<221> NAME/KEY: MOD_RES
<222> LOCATION: (5)..(5)
<223> OTHER INFORMATION: Glu or Ala
<220> FEATURE:
<221> NAME/KEY: MOD_RES
<222> LOCATION: (6)..(6)
<223> OTHER INFORMATION: Gln or Ala
<220> FEATURE:
<221> NAME/KEY: MOD_RES
<222> LOCATION: (7)..(7)
<223> OTHER INFORMATION: Lys or Ala
<220> FEATURE:
<221> NAME/KEY: MOD_RES
<222> LOCATION: (8)..(8)
<223> OTHER INFORMATION: Tyr or Ala
<220> FEATURE:
<221> NAME/KEY: MOD_RES
<222> LOCATION: (9)..(9)
<223> OTHER INFORMATION: Ser or Ala
<220> FEATURE:
<221> NAME/KEY: MOD_RES
<222> LOCATION: (10)..(10)
<223> OTHER INFORMATION: Phe or Ala
<220> FEATURE:
<221> NAME/KEY: MOD_RES
<222> LOCATION: (11)..(11)
<223> OTHER INFORMATION: Leu or Ala
<220> FEATURE:
<221> NAME/KEY: MOD_RES
<222> LOCATION: (12)..(12)
<223> OTHER INFORMATION: Gln or Ala
<220> FEATURE:
<221> NAME/KEY: MOD_RES
<222> LOCATION: (13)..(13)
<223> OTHER INFORMATION: Asn or Ala

<400> SEQUENCE: 14

Tyr Ile Pro Xaa Xaa Xaa Xaa Xaa Xaa Xaa Xaa Xaa Xaa Pro Gln Thr
1               5                   10                  15
```